(12) United States Patent
Altman

(10) Patent No.: US 6,346,099 B1
(45) Date of Patent: Feb. 12, 2002

(54) CATHETER DRUG DELIVERY SYSTEM AND METHOD FOR USE

(75) Inventor: Peter A. Altman, San Francisco, CA (US)

(73) Assignee: Biocardia, Inc., S. San Francisco, CA (US)

( * ) Notice: Subject to any disclaimer, the term of this patent is extended or adjusted under 35 U.S.C. 154(b) by 0 days.

(21) Appl. No.: 09/638,378

(22) Filed: Aug. 12, 2000

Related U.S. Application Data

(63) Continuation of application No. 09/131,968, filed on Aug. 11, 1998, now Pat. No. 6,102,887.

(51) Int. Cl.[7] .................. A61M 25/01; A61M 25/02; A61M 25/04; A61M 25/06; A61M 25/08; A61M 25/082; A61M 25/085; A61M 25/088; A61M 25/09; A61M 26/095; A61M 25/098

(52) U.S. Cl. .................. 604/528; 604/22; 604/95.01; 604/95.04; 604/164.01; 604/272

(58) Field of Search .................. 604/19, 21, 22, 604/27, 500, 506, 507, 93.01, 95.01, 95.04, 508, 158, 159, 164.01, 104.12, 165.01, 264, 523, 528, 272

(56) References Cited

U.S. PATENT DOCUMENTS

| | | | |
|---|---|---|---|
| 2,554,352 A | 5/1951 | Ward et al. ............... 604/200 |
| 2,691,372 A | 10/1954 | Lores ...................... 604/200 |
| 4,994,067 A | 2/1991 | Summers ................. 606/159 |
| 5,002,067 A | 3/1991 | Berthelson ............... 128/786 |
| 5,016,640 A | 5/1991 | Ruiz ....................... 128/658 |
| 5,030,204 A | 7/1991 | Badger et al. ............ 604/95 |
| 5,236,424 A | * 8/1993 | Imran ...................... 604/280 |
| 5,324,325 A | 6/1994 | Moaddeb ................. 607/120 |
| 5,378,234 A | 1/1995 | Hamerslag et al. ........ 604/95 |
| 5,385,148 A | 1/1995 | Lesh et al. ............ 128/662.06 |
| 5,405,376 A | 4/1995 | Mulier et al. ............ 607/127 |
| 5,431,649 A | 7/1995 | Mulier et al. ............ 606/41 |
| 5,441,499 A | 8/1995 | Fritzsch .................. 606/45 |
| 5,447,533 A | 9/1995 | Vachon ................... 607/120 |
| 5,474,543 A | * 12/1995 | McKay ................... 604/272 |
| 5,531,780 A | 7/1996 | Vachon ................... 607/120 |
| 5,542,926 A | 8/1996 | Crocker .................. 604/102 |
| 5,551,427 A | 9/1996 | Altman ................... 128/642 |
| 5,609,151 A | 3/1997 | Mulier et al. ............ 128/642 |
| 5,661,133 A | 8/1997 | Leiden et al. ............ 514/44 |
| 5,698,531 A | 12/1997 | Nabel et al. ............ 514/44 |
| 5,704,910 A | 1/1998 | Humes .................... 604/52 |
| 5,722,400 A | 3/1998 | Ockuly et al. ........... 128/642 |
| 5,873,852 A | * 2/1999 | Vigil et al. .............. 604/52 |
| 5,980,516 A | * 11/1999 | Mulier et al. ............ 606/41 |
| 6,004,295 A | * 12/1999 | Langer et al. ........... 604/164 |
| 6,102,887 A | * 8/2000 | Altman ................... 604/22 |

OTHER PUBLICATIONS

Miller, et al., J. Biomed. Res. 11, 711 (1977).

Putney, et al., Improving Protein Therapeutics with Sustained Release Formulations, 16 Nature Biotechnology 153–57 (Feb. 1998).

Scheinman, Supraventricular Tachycardia: Drug Therapy Versus Catheter Ablation, 17 Clinical Cardiology II–II (1994).

* cited by examiner

*Primary Examiner*—Glenn K. Dawson
*Assistant Examiner*—Jennifer Maynard
(74) *Attorney, Agent, or Firm*—K. David Crockett, Esq.; Crockett & Crockett

(57) ABSTRACT

A catheter system for injecting therapeutic agents including large molecules into the body. The catheter includes a distensible penetrating element with a distally locating expansion coil and a distally located chamber for holding a therapeutic agent which is to be injected into the body.

6 Claims, 9 Drawing Sheets

CATHETER DRUG DELIVERY SYSTEM AND METHOD FOR USE

RELATED PATENT APPLICATION

This application is a continuation of application Ser. No. 09/131,968, filed Aug. 11, 1998, now U.S. Pat. No. 6,102,887, issued Aug. 15, 2000.

FIELD OF THE INVENTION

The present invention relates to devices for local delivery of therapeutic agents for use within a body tissue.

BACKGROUND OF THE INVENTION

Catheter systems for local delivery of therapeutic agents have many advantages. Approaches for local delivery of agents at a depth within a tissue are applicable to the heart, pancreas, esophagus, stomach, colon, large intestine, and other tissues which may be accessed via a catheter system. These catheter systems will deliver drugs to the sites where they are most needed, reduce the amount of drug required, increase the therapeutic index, and control the time course of agent delivery. These, in turn, improve the viability of the drugs, lower the amount (and cost) of agents, reduce systemic effects, reduce the chance of drug-drug interactions, lower the risk to patients, and allow the physician to more precisely control the effects induced. Such local delivery may mimic endogenous modes of release, and address the issues of agent toxicity and short half lives.

Local drug delivery to the heart is known. In U.S. Pat. No. 5,551,427, issued to Altman, implantable substrates for local drug delivery at a depth within the heart are described. The patent shows an implantable helical injection needle which can be screwed into the heart wall and connected to an implanted drug reservoir outside the heart. This system allows injection of drugs directly into the wall of the heart acutely by injection from the proximal end, or on an ongoing basis by a proximally located implantable subcutaneous port reservoir, or pumping mechanism. The patent also describes implantable structures coated with coating which releases bioactive agents into the myocardium. This drug delivery may be performed by a number of techniques, among them infusion through a fluid pathway, and delivery from controlled release matrices at a depth within the heart. Controlled release matrices are drug polymer composites in which a pharmacological agent is dispersed throughout a pharmacologically inert polymer substrate. Sustained drug release takes place via particle dissolution and slowed diffusion through the pores of the base polymer. Pending applications Ser. No. 08/881,850 by Altman and Altman, and Ser. No. 09/057,060 by Altman describes some additional techniques for delivering pharmacological agents locally to the heart.

Local drug delivery has been used in cardiac pacing leads. Devices implanted into the heart have been treated with antiinflammatory drugs to limit the inflammation of the heart caused by the wound incurred while implanting the device itself. For example, pacing leads have incorporated steroid drug delivery to limit tissue response to the implanted lead, and to maintain the viability of the cells in the region immediately surrounding the implanted device. U.S. Pat. No. 5,002,067 issued to Berthelson describes a helical fixation device for a cardiac pacing lead with a groove to provide a path to introduce anti-inflammatory drug to a depth within the tissue. U.S. Pat. No. 5,324,325 issued to Moaddeb describes a myocardial steroid releasing lead whose tip of the rigid helix has an axial bore which is filled with a therapeutic medication such as a steroid or steroid based drug U.S. Pat. Nos. 5,447,533 and 5,531,780 issued to Vachon describe pacing leads having a stylet introduced anti inflammatory drug delivery dart and needle which is advanceable from the distal tip of the electrode.

Local drug delivery has been described also for cardiac ablation. The acute infusion of different fluids to a depth within the myocardium has been described in the patent literature as being useful for ablation. U.S. Pat. Nos. 5,405, 376; 5,431,649; and 5,609,151 issued to Mulier describes a hollow helical delivery needle to infuse the heart tissue with a conductive fluid prior to ablation to control the lesion size produced. U.S. Pat. No. 5,385,148 issued to Lesh describes a cardiac imaging and ablation catheter in which a helical needle may be used to deliver fluid ablative agents, such as ethanol, at a depth within the tissue to achieve ablation. Another system for delivery of chemical agents to tissue has been described by Imran in U.S. Pat. No. 5,236,424 in which steerability and deployment of the active structures require electrical energy.

No one has solved the problem of providing a mechanically deployable tissue penetrating element to an infusion catheter. Lesh has described his device as deployable, but he does not describe the actual design of elements, nor does he enable its manufacture. He does not describe how his hollow helical tissue penetrating needle element advances and rotates without disconnecting it from its fluidic pathway. Mulier apparently recognized these problems, and avoided the issue by described his system as being advanceable down a guiding catheter system. In addition, neither of these systems was intended for the delivery of therapeutic agents. Altman, in pending U.S. application Ser. No. 09/057,060 has described an approach for using a distensible coil of tubing located at the distal end of the infusion catheter, which will be developed further here. There is a need for controlled deployment of penetrating hollow elements such as needles and helixes for infusion of therapeutic agents to a depth within tissue.

No one has solved problems of combining drugs and devices at time of use. The prior art describes approaches for delivering agents from the proximal end of a long catheter using a fluidic pathway, or from part of the manufactured device, such as a polymer controlled release matrix. The end to end fluidic delivery may reduce the accuracy of dose delivery, and may potentially alter the viability of therapeutic agents by either material contamination or shear stresses experienced during passage of the fluidic agent or micro drug delivery slurry down the catheter body. There is a need for combining small amounts of therapeutic agents to catheter systems at the catheter distal ends a the time of delivery. This will allow therapeutic agents to be stored separately from the devices, and reliably combined at the time of delivery. Although pending application Ser. No. 08/881,850 by Altman and Altman does describe some techniques which address this issue, such as clearable fluid pathways, additional solutions are needed.

No one has solved the problem of providing steerability to an infusion catheter with a deployable element. Lesh has described the need for steerability, but does not provide ways for mechanical steerable elements, such as bending ribbons, to be constructed to provide room for the larger fluid conduit to pass undamaged. By having his pull wires for steerability attached to the distal-most region of the disclosed catheter system, a curve will be imparted into the portion of the distal region of the catheter that houses the deployable element. This is problematic and may cause bending of the deployable element, thus preventing its deployment. There is a need to provide a steerable catheter with a deployable element for infusion which does not bend the deployable element during steering. Further, there is a need for a mechanical steerable infusion catheter which allows for steering structures such as bending ribbons with large openings to prevent kinking and damage of the infusion tubing.

There is also a need to provide for rapid deployment and retraction of the penetrating infusion structure for reducing the duration of the catheterization procedure. Similarly, there is also a need for a system that will rapidly re-position the catheter in a controlled manner for multiple infusions at set locations relative to one another.

SUMMARY

The drug delivery catheters described below provide a distensible penetrating element such as a helical needle or straight needle within the distal tip of the catheter. The penetrating element is coupled to a reservoir or supply line within the catheter so that drugs and other therapeutic agents can be injected through the penetrating element into the body tissue which the element penetrates. In use, the drug delivery catheter is navigated through the body to the organ or tissue to be treated, the penetrating element is advanced from the distal end of the catheter, and a therapeutic agent is delivered through the penetrating elements into the organ of tissue. For example, the device may be navigated through the vasculature of a patient into the patient's heart, where the penetrating element is advanced to cause it to penetrate the endocardium, and an anti-arrhythmic drug or pro-rhythmic drug can be injected deep into the myocardium through the penetrating element.

BRIEF DESCRIPTION OF THE DRAWINGS

FIG. 2a is a radial cross section of the segment of the drug delivery catheter illustrated in FIG. 2.

FIG. 6a is a cross section of the catheter illustrated in FIG. 6.

FIG. 9 illustrates a proximal operating handle for the catheters illustrated FIG. 8a.

DETAILED DESCRIPTION OF THE INVENTION

Figure 1:
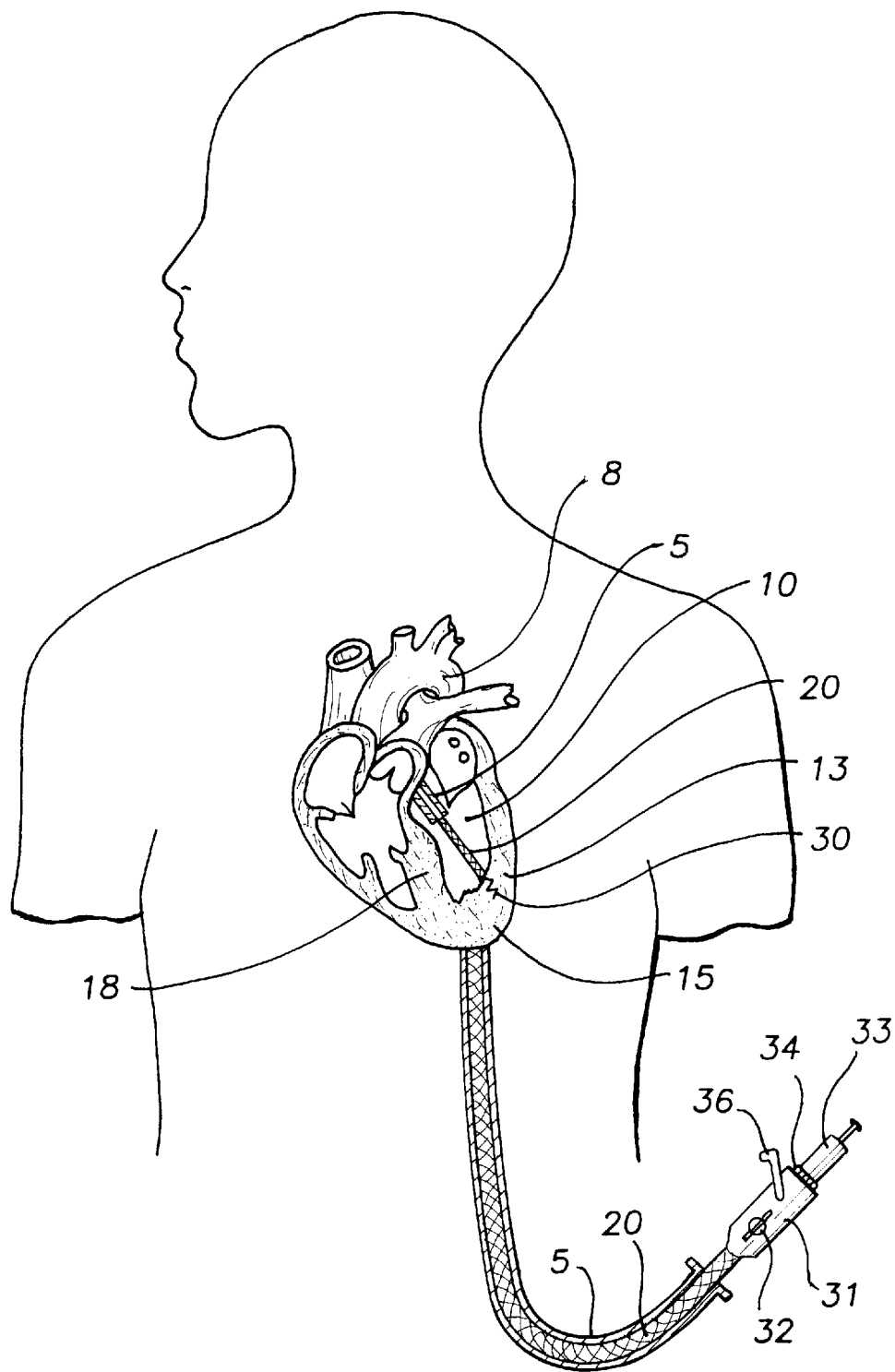
FIG. 1 is an illustration of the drug delivery catheter in an exemplary use within the heart of a patient.

FIG. 1 shows an overview of a left ventricle (LV) drug delivery catheter with a guiding catheter system. Guiding catheter 5 is advanced through the arterial system through the aorta 8 and through the aortic valve into the left ventricle 10. The steerable drug delivery catheter 5 has a deployable distally penetrating structure 30 that allows for fluid agents or agents in fluid suspension to be delivered to a depth within the heart wall. The penetrating structure 30 is shown to be a hollow helical needle for securing the delivery catheter to prevent misplacement which may result because of the motion of the beating heart. The drug delivery sites may be in the left ventricular free wall 13, the left ventricular apex 15, or the ventricular septum 18. In other embodiments the penetrating structure could incorporate a solid helix, a hollow centrally located needle, a solid straight centrally located needle, curved needles, engagement pinchers or crossing penetrating needle structures, or appropriate combinations of these structures.

The proximal end of drug delivery catheter is shown here to end in a steerable catheter handle 31 that incorporates a knob 32 to apply tension to one or more pull wires within steerable catheter 5, in addition to a proximally located luer lock 34 shown connected to drug delivery syringe 33. The luer 34 enables drugs to be injected throughout the length of the catheter 5, or it allows a pressurized fluid to be injected to operate a distal drug reservoir (see FIG. 4). The luer could also be placed distal to the handpiece. The pull wires controlled by knob 32 do not connect to the distal most region of the catheter body tubing, as it is important that the distal most region housing the deployable element remain straight.

Coil rotation handle 36 connects within the handle to a torque coil (not shown) for rapid advancement and retraction of the helical needle penetrating drug delivery structure shown here. This crank connects to a coil in the handle which undergoes a gradual bend to provide for rotation of the distal penetrating coil by the implanting physician.

Figure 2:
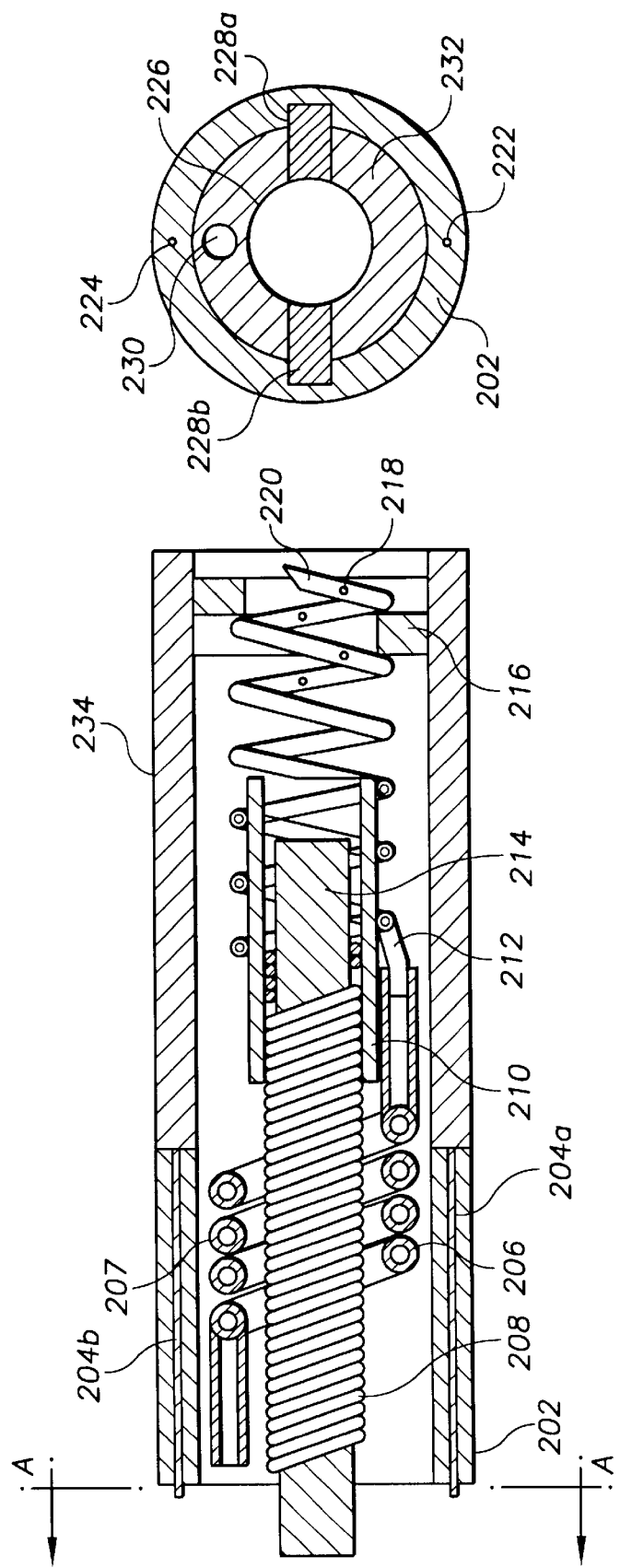
FIG. 2 is a cross section of the distal tip of the drug delivery catheter with a helical distensible penetrating element.

FIG. 2 shows a partially sectional view of the steerable drug delivery catheter shown in FIG. 1. A deployable hollow helical needle 220, which may have apertures 218 along a small portion of its distal most region, forms a distally extendable penetrating element. The helical coil is connected to a drug delivery tubing 206 at proximal end of hollow helical needle 212. Drug delivery tubing is formed of materials that will not affect the drug component or micro delivery systems such as nylon, polyethylene, polyurethane, or polytetrafluoroethylene. A flexible torque transmitting shaft is provided in the form of torque coil 208 with centrally located stylet 214 enables deployment of the helical needle 220 by rotation of the stylet in the torque transmission tube 210 which forces the helix to deploy through the inside threads 216 which operably mate with the helical coil. The inside threads 216 engage the helical coil like to cause a screw-action when the helical coil is turned by rotation of the torque coil 208. The stylet and torque transmission tube create a rotatable and longitudinally extendable mechanical element which transmits force applied by the operating surgeon to the distally located penetrating element. Therapeutic fluidic agents may be forced by a proximally located pressure source to flow down drug delivery tubing 206 which is shown coiled here around the torque coil 208 to allow it to distend when helical needle 220 is advanced. The coiled segment 207 of the delivery tubing 206 creates a longitudinally expandable or distensible fluid conduit which connects the distally extending helical coil to the delivery tubing. The deployable hollow helical needle 220 is wound in the opposite direction to the coiled drug delivery tubing 206. In this figure, the penetrating helix is said to be a left hand wound structure, and the drug delivery tubing is a right hand wound structure. Their handedness could easily be reversed. It is important that they be wound in opposite directions because the rotational advancement of the penetrating structure 220 will essentially peel off a sufficient amount of the coiled tubing 206. Pull wires 204a and 204b do not attach to the distal-most region of the catheter. Instead, they are fixed at their distal ends to the catheter at a point near the proximal end of the extendable penetrating element (in this case the helical coil 220). The distal most region of the catheter in which the helical coil is housed will not bend in response to pull wire activation. This prevents the pullwires from imparting a bend or a bending moment on the distal catheter body tubing 234 which houses the deployable penetrating drug delivery element, shown here as helical needle 220, which in turn would bind the penetrating element and hinder deployment.

FIG. 2a shows a cross sectional view is proximal to the end of the catheter body region shown with the stylet 214 and coil 208 removed. The catheter has a tri-lumen tubing body 202 with small lumens 222 and 224 in its wall. The small lumens 222 and 224 house the pull wires or cables 204a and 204b which enable the catheter to be deflected. Split bending ribbons 228a and 228b are positioned with their long dimension at right angles to the plane of bending, such that the plane of bending has a reduced bending rigidity as compared to all other potential bending planes. This is important in that it provides the catheter with a reliable and repeatable bend geometry. Attached to the split bending ribbons 228a and 228b is a guide tubing 232 which stabilizes the two bending ribbons, provides a controlled pathway 230 for the drug delivery tubing to pass through the critical bending region, and provides for unobstructed rotation of the centrally located torque transmission coil 208 in central lumen 226 of guide tubing 232. No other such split bending ribbon system is known in the prior art. The region shown does not contain the coiled drug delivery tubing. Thus, it is clear that with such approaches, a plane of bending can be clearly defined in a bi-directional steerable catheter with an independent drug delivery tubing which can be distended to allow a deployable penetrating structure to deliver a fluidic agent to a depth within a body tissue.

Figure 3:
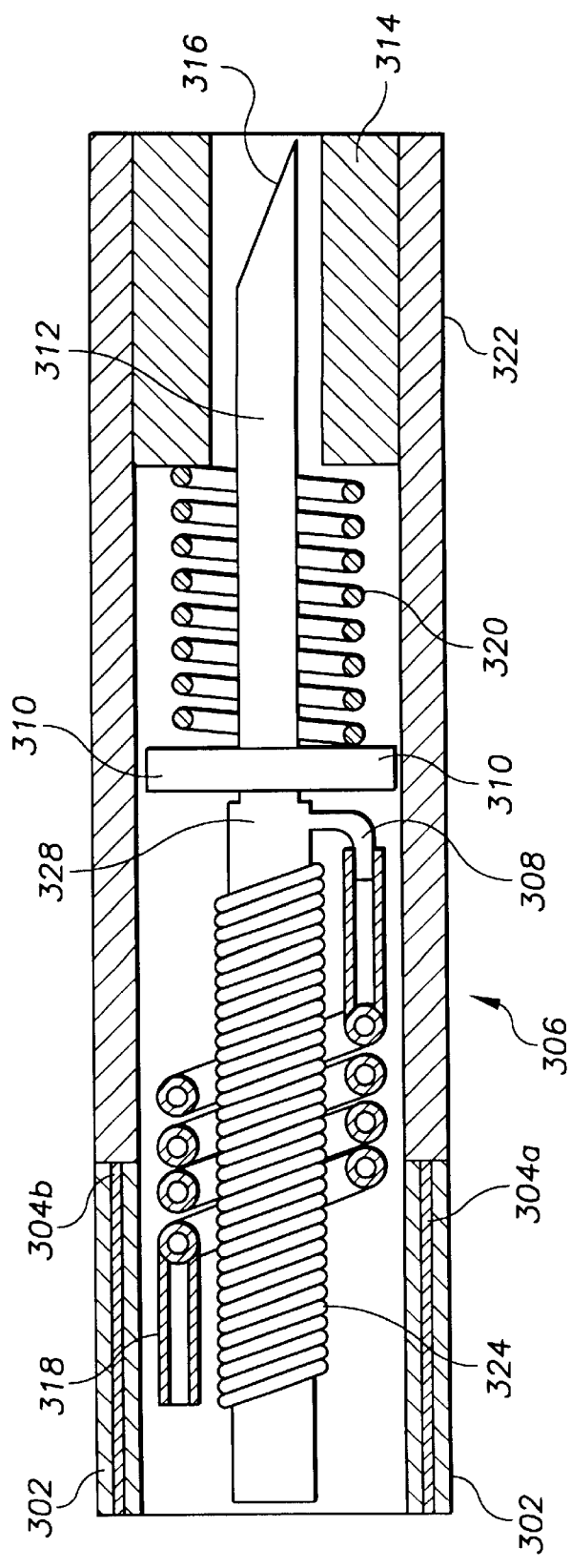
FIG. 3 is a cross section of the distal tip of a drug delivery catheter with a straight distensible penetrating element.

FIG. 3 shows the distal end of a similar bi-directional fluid delivery steerable catheter with two pull wires 304a and 304b attached to the distal end of the main catheter body 302. Distal catheter body 322 is bonded or molded to the end of tri lumen tubing 302 using known techniques and tubing joint constructions. Here, the penetrating structure is a simple straight hollow 316 LVM stainless steel needle 312 with penetrating tip 316. Once positioned, such as at the left ventricular free wall, a stylet is advanced down centrally located coil to drive the needle 312 into the tissue, to a depth controlled by end stops 314. Distending helical fluid delivery tubing 318 which connects to hollow needle fitting 308 in region 306. Once the stylet has forced the needle 312 into the tissue, such as the myocardium, the fluid tubing 318 may be used to deliver therapeutic agents to a depth within the tissue. In this embodiment, the system is made with a distal spring 320 to automatically retract the needle from penetrating the tissue after pressure from the stylet is released. Force applied to coil pin 328 from stylet and coil allow force transmission to the needle 312 and compression of spring 320 via spring plate 310. Spring 320 may be removed in various embodiments.

In other applications, the advancement of the needle to a depth within the heart wall could be configured to trigger a pressure source to deliver a set pressure pulse or positive displacement of fluid to automatically deliver a therapeutic agent to a depth within the heart wall. This could be accomplished with a switch which is closed by the advancement of the stylet relative to the catheter handpiece on the proximal end. Such a mechanism would be useful for rapid delivery to the beating heart, and could also be used if more than one delivery site was to be used. The system would be positioned, and the process of needle advancement to penetrate the heart wall would trigger the delivery of therapeutic agent.

Figure 4A:
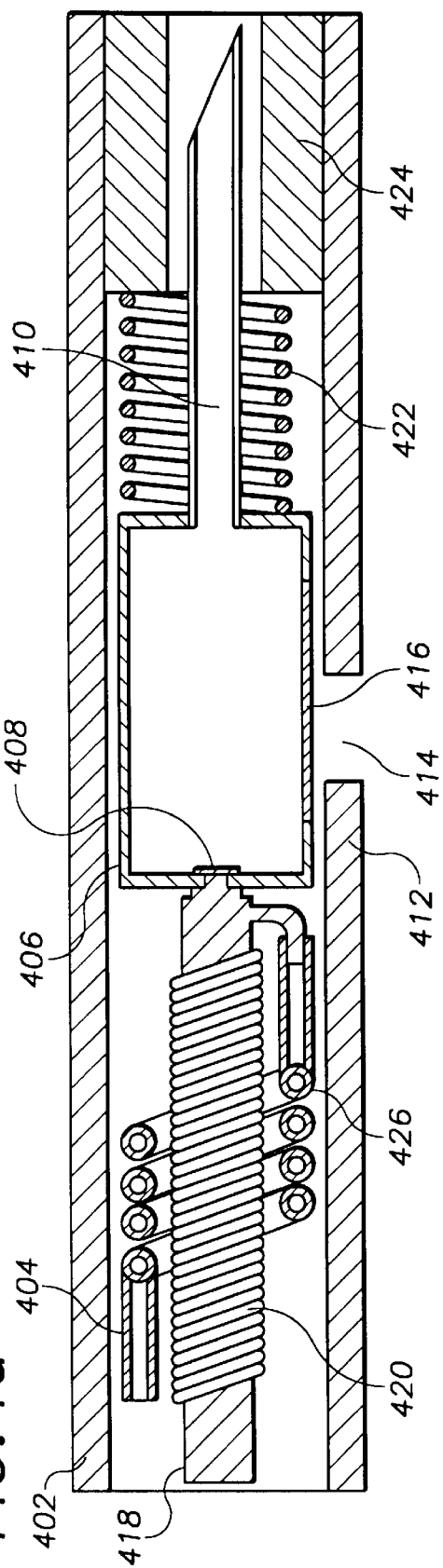
FIGS. 4a and 4b is a cross section of the distal tip of a drug delivery catheter with a reservoir for holding therapeutic agents for delivery through the penetrating element.

FIG. 4a shows a catheter similar to that shown in FIG. 3. It is bi-directionally steerable and has a deployable penetrating element. This catheter system is shown in partial cross section 90 degrees off of the plane defined by the pull wires. For this reason, no pull wires are shown. In this partially sectional view, catheter body 402 is shown to have a hole 414 at catheter body distal region 412 to facilitate the micro-injection of therapeutic fluid or slurry of therapeutic agents in fluid suspension to a small delivery chamber 406 which could be formed of Titanium or epoxy. In filling chamber 406, a small syringe is passed through hole 414 in catheter body 412 and penetrate a self-sealing membrane barrier 416 of small delivery chamber 406 (the membrane may be made of silicone or various other materials that may be penetrated with a needle and seal themselves when the needle is removed). If desired, the delivery chamber can be pre-filled before it is filled with a second therapeutic agent. Such an initial fluid agent could be transported through fluid delivery tubing 404, into fitting 426, and through optional check valve 408 to fill the small drug delivery chamber 406. After the system is filled with a first fluid, a second fluid is injected into chamber 406 through polymer barrier 416 which is formed of silicone or other self sealing membrane. Injection of at least one component of the therapeutic agent into the chamber eliminates the need to force that agent through the entire length of the catheter before reaching the target site. This limits the stress placed on the therapeutic molecules, and also eliminates the need to fill the entire catheter with the therapeutic agent prior before it starts coming out of the distal end of the catheter.

Once in position at in interior body surface, such as the endocardium of the left ventricle free wall, force is applied by a removable stylet 418 within coil 420 to force chamber 406 to compress spring 422 and allow needle 410 to penetrate through end of catheter 402 a distance controlled by depth control 424. After the needle penetrates the tissue to a depth, fluid in fluid delivery tube 404 is pressurized and driven through now elongated coiled fluid delivery tube 426 and through the check valve 408 to force the therapeutic agents within chamber 406 through the needle 410 and into the heart wall. Such a fillable distal chamber may be coupled with distally located drug delivery systems such as osmotic pumps and controlled release matrices such as are described in pending application Ser. No. 08/881,685 by Altman and Altman.

This same overall catheter design could be used in other applications where there is no need to fill the distal chamber 406, and therapeutic fluidic agents are delivered from proximal end to distal end. The therapeutic agent would be delivered from one end of the catheter to the other without concern for the distal fillable reservoir.

Figure 4B:
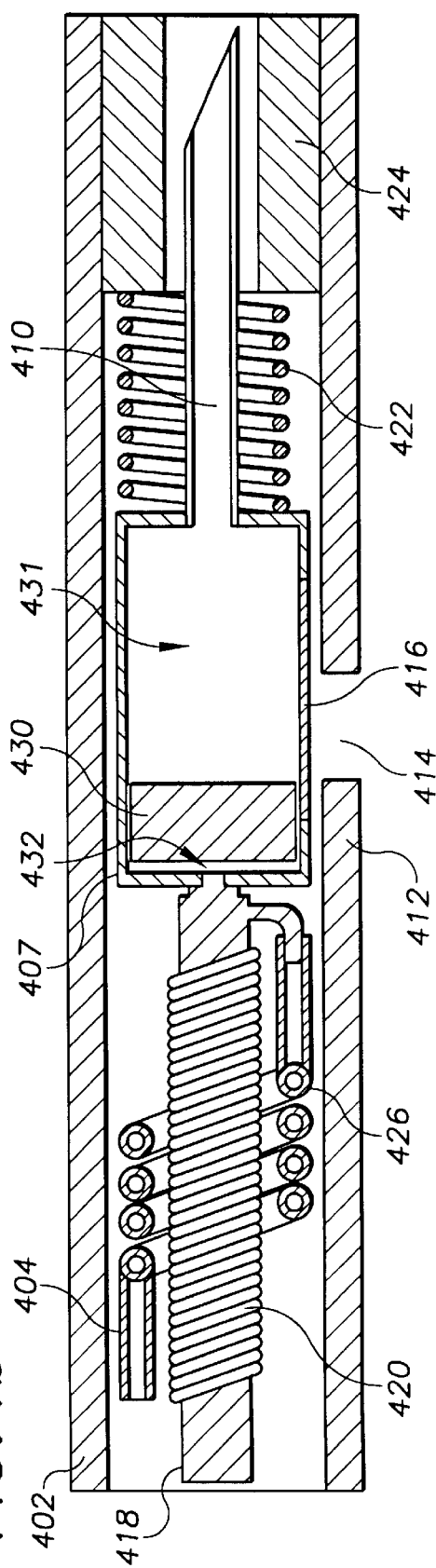

FIG. 4b illustrates a drug delivery system incorporating a piston chamber which us used to drive the therapeutic agents from the chamber. The piston chamber 407 includes a piston 430 which divides the chamber into a distal chamber 431 and proximal chamber 432. The distal chamber is filled during manufacture or by injection through the silicone membrane 416. The therapeutic agents are ejected from the chamber by injecting a fluid into the proximal chamber, through the delivery tube 404 and check valve 408. The pressurization of the proximal chamber forces any fluid in the distal chamber through the needle 410 and into the body. The piston may also be driven by a stylet 418 passing into the and forcing the piston distally.

Further, similar to the description of FIG. 3, the application of force by the stylet mechanism could be used to trigger a proximally located pumping source to coordinate the penetration of the heart endocardium by the fluid delivery needle and the delivery of fluid through the needle.

Figure 5:
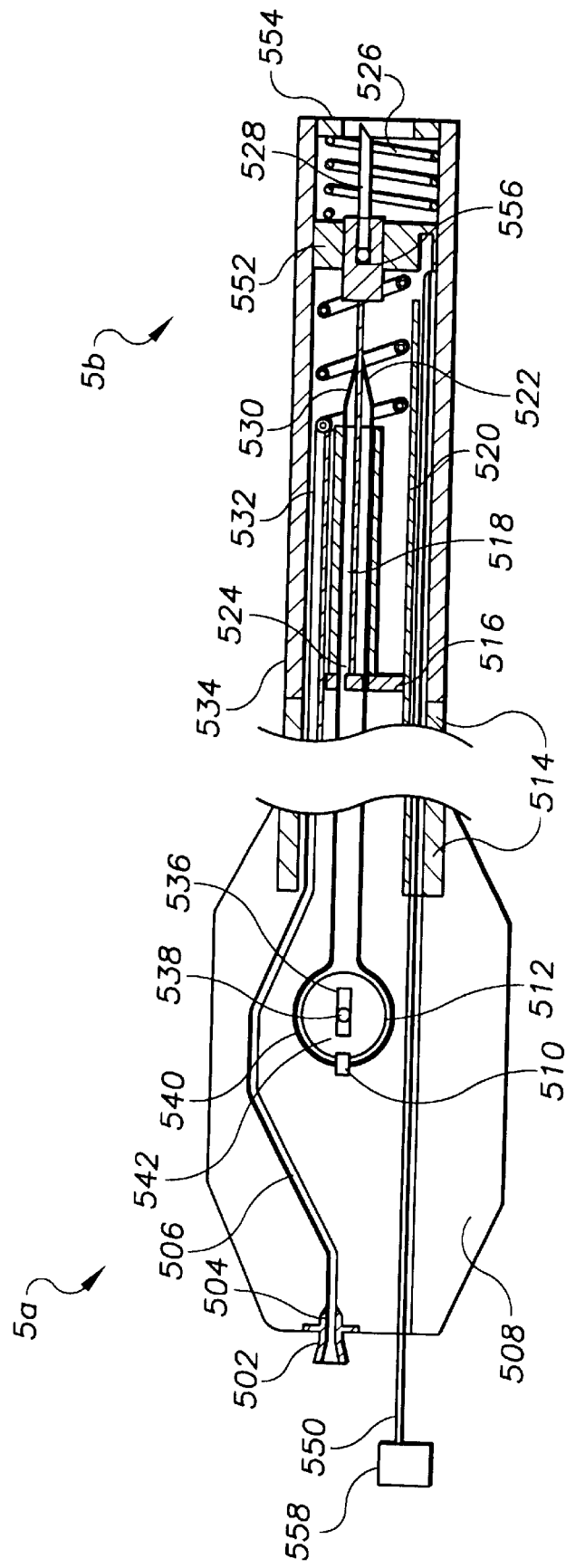
FIG. 5 is a cross section of a drug delivery catheter with a pullwire steering mechanism which operates on the near distal segment of the delivery catheter which is just proximal of the distensible mechanism for deploying the penetrating element from the catheter.

FIG. 5 shows another embodiment of a steerable catheter encompassing two centrally located pull wires 540 and 512 as opposed to the more radially located pull wire systems described so far. Here, the distally located penetrating needle structure 528 is spring loaded in a retracted position with distally located spring 526. The spring element 526 is compressed by an advancing stylet 550 from the proximal end of the catheter system for delivering agents to a depth within the heart. Advancing stylet 550 is fully removable and advanced from the proximal end to engage force transmission part 552 which holds needle support structure 556. Once in position against force transmission part 552, spring 526 is compressed by pressing on stylet knob 558. Stylet 550 is shown advancing down a second lumen 520 in tubing 534 and 514, although in other embodiments it may pass down a dedicated tube or coil within the larger catheter body.

Distal end 5b shows that fluidic agents may travel the length of the catheter through drug delivery tubing 532 to be delivered to a depth within the tissue through needle 528 or other similar penetrating drug delivery structure. Within the catheter body, there are also two pull wires 530 and 522 attached to opposite sides of flat metal ribbon 518. Metal ribbon 518 is approximately 0.035" in width and 0.010" thick such that it has much higher bending rigidity in one direction. This enables pulling on one wire to deflect the ribbon quite readily in its direction of low bending rigidity without introducing twisting. The proximal end 524 of ribbon 518 is secured to a fitting 516 with apertures to allow the passage of both the pull wires 530 and 522, and the drug delivery tubing 532, but fixes the ribbon in position to the catheter body 534.

Proximal end 5a shows the proximal handle mechanism used to pull the wires 530 and 522 in order to cause a deflection of the distal tip of the catheter. 5a and 5b are separated by a space which denotes that there is a substantially long length of catheter between them in order to advance the distal end to a position within the body. One example is accessing the left ventricular chamber of the heart from a site such as the femoral artery. Proximal end 5a consists of a rigid plastic clamshell handle schematically shown as 508 which fits over the proximal catheter body 514. Proximal catheter body 514 may be much more rigid than distal catheter body 534 in order to increase the localization of the deflection to the distal end upon pulling on one of the pull wires 530 or 522. Pull wires are connected to a rotating disk 542 at crimp block 510. Distal wires 530 and 522 are shown wrapped around disc 542 as 540 and 512, respectively. The disc 542 rotates around its center and can be deflected by a rotation of knob 538 which can be actuated from outside the clamshell handle. Rotation of the disc in one direction will apply tension on one pull wire and slack on the other pull wire. In this way the distal end of the catheter will be deflected. Tubing 506 travels through the handle 508 and is continuous with the drug delivery tubing 532 in the catheter body. On the proximal end of the handle, tubing 506 connects to proximal luer lock 502 with clamshell fitting 504 such that a syringe may be used to deliver a therapeutic agent to the distal end of the steerable catheter system and to a depth within the heart wall through needle 528.

Although not shown in FIG. 5, the crank 36 that appears in FIG. 1 could be incorporated to protrude on the most proximal end of the handle adjacent to the luer infusion port 502. Such a crank would enable rapid application of torsion to the torque coil for retraction and advancement of the helical penetrating infusion systems. The crank could be placed in many locations on such a handle because the coil structure is quite able to transmit torque around bends. The pull wire mechanism shown could also be used with any of the catheter systems shown here.

Figure 6:
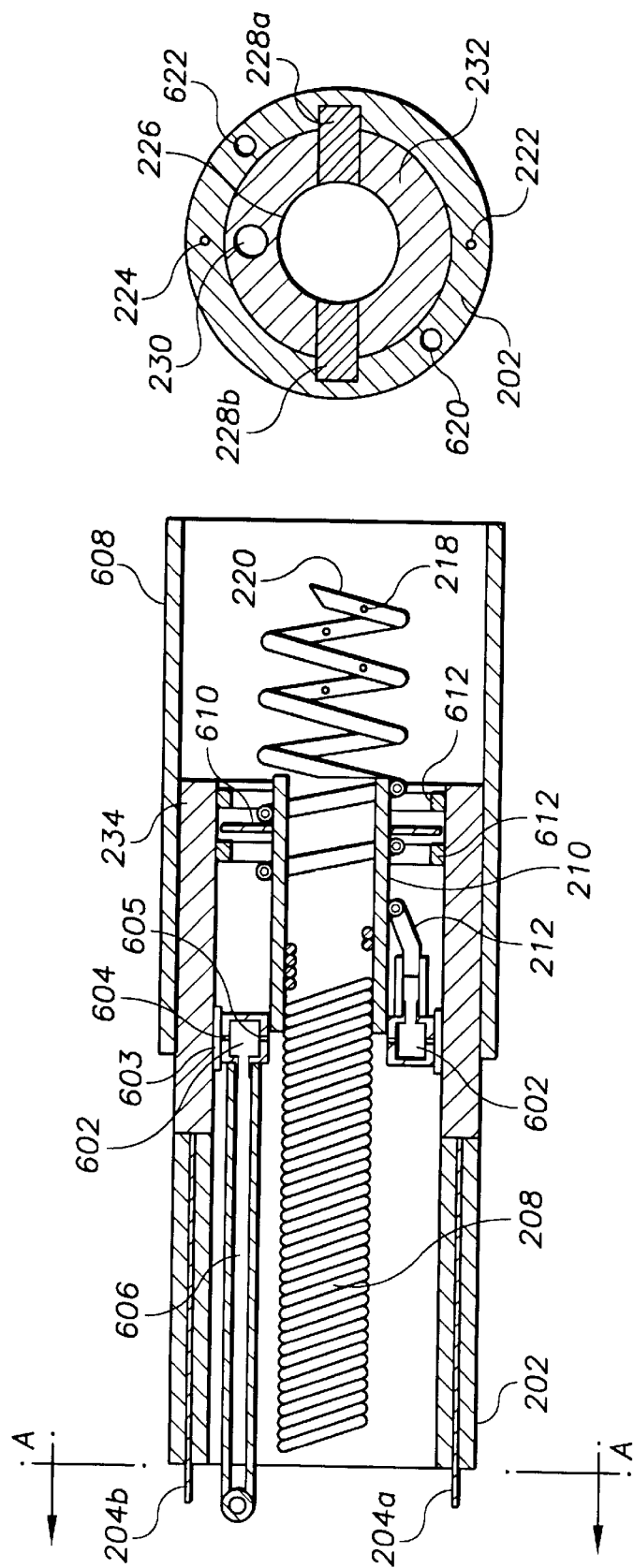
FIG. 6 is a cross section of the distal tip of a drug delivery catheter with a pullwire steering mechanism which operates on the near distal segment of the delivery catheter and a rotatable fluid coupling.

FIG. 6 shows an alternative effectively deployable catheter that is similar to the catheter of FIG. 2. The components catheter body 202, the coiled tubing, pullwires 204a and 204b, the helical needle 220 are the same as the corresponding components of FIG. 2. Instead of deploying, helix 220 is exposed from the end of the catheter by the retraction of covering sleeve 608 which is activated by two separate pull wires(not shown). Sleeve pull wires are shown to travel down catheter body lumens 620 and 622 which are opposite one another and 45 degrees off axis from either the split bending ribbon 228a and 228b or the steerable pull wire lumens 224 and 222.

In this embodiment, the helical needle 220 does not move axially with respect to the catheter body 202, but only rotates in rotation track 612 which surrounds circular disk 610 which is attached to torque transmission tubing 210, such that rotation of the single or bi-directional torque coil 208 on the proximal end of the catheter (not shown) will rotate the helix 220. Fluid continuity through tubing 606 to helix 220 is maintained by a rotatable fluid compartment 602 with dual o-ring seals 604 and dual o-ring seals 605. This enables torque to be applied to the distal drug delivery helix 218 for advancement and retraction, while the patency of the fluid pathway is maintained. To help stabilize the configuration of the rotatable seal, it is bound to the catheter body tubing with adhesive 603 and welded at its distal rotating half to the torque transmission tubing. Other rotatable seals are also possible.

It is clear that if the penetrating element were a straight needle, no rotatable seal would be required, and all of the embodiments described in FIGS. 3, 4, and 5 could be reduced to practice with a retractable sheath. Further, in these applications the distensible fluid conduit, and the coiled stylet guide could be removed. FIG. 6a shows a cross section of the catheter of FIG. 6 on plane A—A, in the portion containing the pullwires. The pull wires used for retracting the sleeve 608 travel down catheter body lumens 620 and 622, arranged on opposite sides of the catheter wall. Lumens 620 and 622 are opposite one another and 45 degrees off axis from either the split bending ribbon 228a and 228b or the steerable pull wire lumens 224 and 222.

Figures 7, 7A:
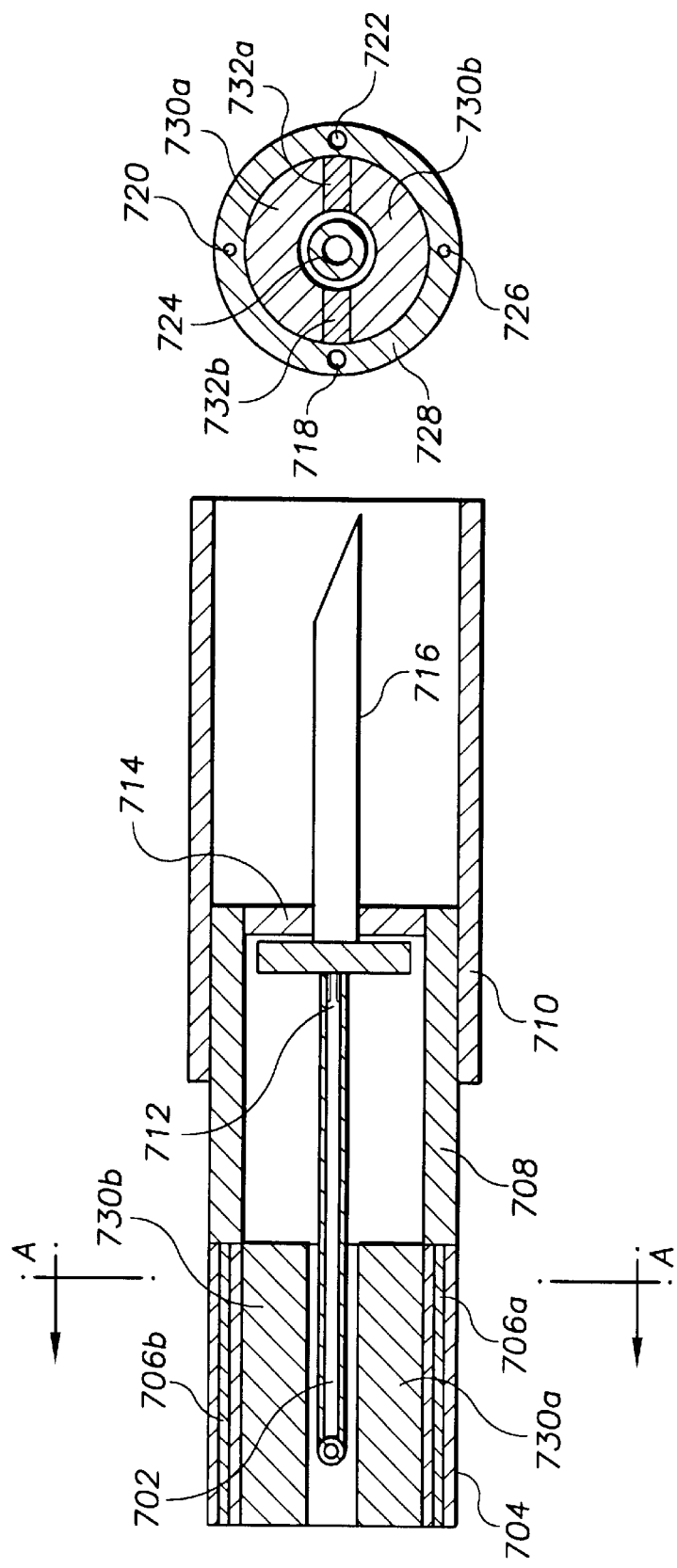
FIG. 7 is a cross section of the distal tip of a drug delivery catheter.
FIG. 7a is a cross section of the catheter illustrated in FIG. 7.

FIG. 7 shows such a bi-directional effectively deployable catheter. Here, pull wires 706a and 706b in main catheter tubing body 704 are as before and terminate proximal to the deployable drug delivery elements encased in distal single lumen tubing 708. These steerable pull wires pass through outer lumens 720 and 726, while the pull wires to retract the sleeve 710 which covers the penetrating element, shown here as hollow needle 716 pass through outer lumens 718 and 722. These sleeve pull wires are likely attached to a larger structure, such as a cylinder which has been molded into sleeve 710 for strength, or pressed into a pre-molded groove and bonded into place. Central drug delivery tube 702 connects to the penetrating needle at fitting 712 and enables a very small dead space to exist on a more robust catheter. Further, the spacing between catheter body 704 internal diameter and drug delivery tubing 702 outer diameter, shown in cross section as 728 and 724, prevents the possibility of having one tubing bind against the other and compromising the patency of the fluid pathway. The low modulus support tubings 730a and 730b sandwich the split bending ribbons 732a and 732b and provide stability to the drug delivery tubing 724. FIG. 7a shows the catheter of FIG. 7 in radial cross section A—A. The support tubings 730a ad 730b traps the bending ribbons 732b and 732b to prevent twisting and slippage of the bending ribbons, the pullwire lumens are located 90° offset from the bending ribbons. Retention sleeve pullwire lumens 718 and 722.

The pull wires for retraction of the sheaths in FIGS. 6 and 7 could also be replaced by sheath structures which cover the catheter bodies from end to end and are in common usage for stent deployment.

Figure 8A:
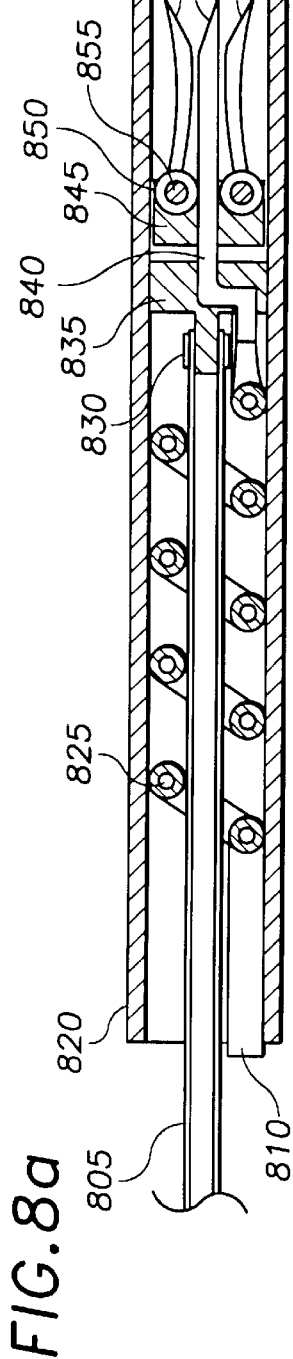
FIGS. 8a through 8c illustrate a penetrating catheter with prongs for attaching the catheter to an injection site.

FIG. 8a shows another embodiment for catheter delivery of therapeutic agents to a depth within a body tissue. FIG. 8 shows a catheter 820 which houses a hollow tube 805 which can accommodate a stylet. The hollow tube terminates in a sliding needle base 835, which is slidably mounted within the catheter 820. A penetrating needle 865 is mounted on the needle base, and communicates through the needle base to the drug delivery tube 810. Also housed within the distal tip of the catheter 820 is an expanding prong fixation system including prongs 860 and 870 and a pivot base 845 which is fixedly mounted on the needle (and slidably disposed within the catheter 820). The prongs are designed to penetrate the body tissue and spread apart when the penetrating drug delivery element (the needle 865) advances axially out the distal end of the catheter body and into the body tissue to be injected. Prongs 860 and 870 are attached at pivots 850 secured by pivot shaft 855. The prongs are radially flared at their distal tips, and therefore are forced to spread radially outwardly when pushed distally from the catheter into body tissue.

The prong structures shown here are sharpened at their distal most ends for piercing the body tissue where the penetrating drug delivery element (the needle 865) is desired to adhere. It also possible that the prongs be made of a softer more blunt structure that is not designed to penetrate the tissue, but merely to grasp or become entangled with tissue surrounding the target penetration site. For example, high durometer polymer material, such as polyurethane could be formed into structures that would stabilize the penetrating element and possibly adhere to surrounding structures such as the trabeculae in the endocardial region of the heart.

Figure 8B:
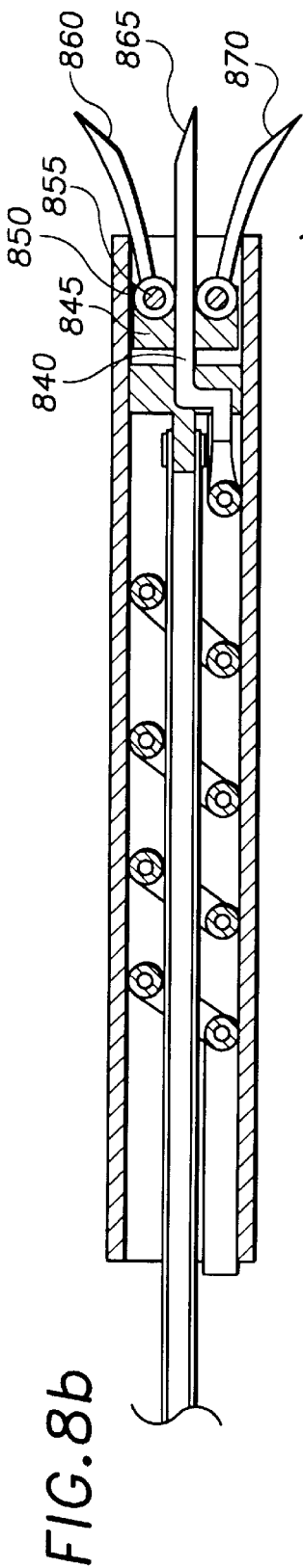
Figure 8C:
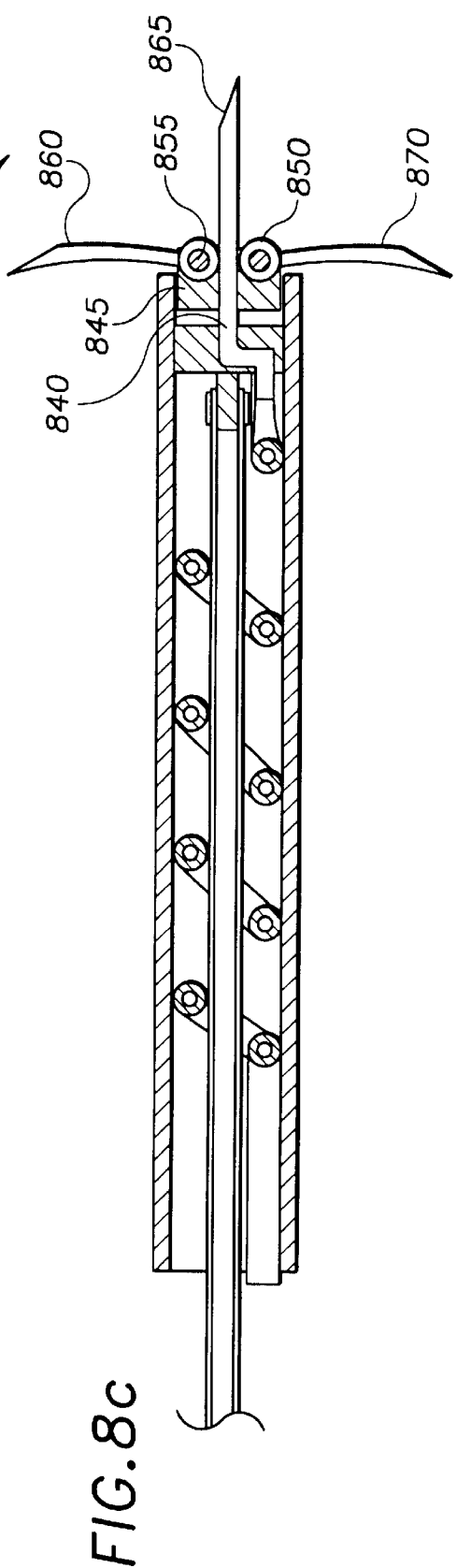

Deployment of the penetrating element shown in FIG. 8a is achieved by advancing a stylet or stiff wire (not shown) down stylet guide coil 805 which runs parallel to the drug delivery tube 810 shown wrapped around coil 805 in a helical section 825 (shown in cross section). The stylet will apply force to needle base 835 which is mechanically crimped to coil 805 with crimp sleeve 830 and provides mechanical support for both the penetrating needle 865, but also the connection of the drug delivery tubing 810 to the proximal offset portion of needle 865. As shown in FIG. 8b, upon advancement of the sliding needle base 835, pivot base 845 which is press fit over needle 865 also advances axially, and the helically coiled section 825 of the drug delivery tubing 810 distends or spreads slightly. FIG. 8b and FIG. 8c illustrate the advancement of the needle and needle base assembly out of the distal tip 875, and the corresponding advancement of the pivot base and prongs out the distal tip of the catheter to allow the prongs to first penetrate the body tissue surface, and then spread radially outwardly from the catheter tip into the surrounding body tissue. As shown in FIG. 8c, when the needle is force entirely out of the distal end of the catheter, the prongs are oriented radially to the catheter axis, and therefore grasp the body tissue surrounding the injection site, holding the needle distal tip at a depth with the target body tissue. It should be noted that it is not necessary to have a complete deployment to have satisfactory delivery of the penetrating element. Further, although only two prongs are shown in FIG. 8, it is very easy to have three or four prongs which behave in a similar fashion at spacings of 120 degrees, and 90 degrees from one another, respectively.

The spreading of prongs 860 and 870 in FIG. 8 is dependent upon shape of the structure as it penetrates the tissue, but in other embodiments it could be controlled by placing a structure at the distal most end of the catheter which would force them apart. Such a distally located structure could easily be used to effect a shape similar to that shown in FIG. 8b. In addition, the needles could be formed of a shape memory material such as nitinol so that once released from the confines of the catheter body 820 they take on the curved shape shown, or even more drastic curves.

Figure 9:
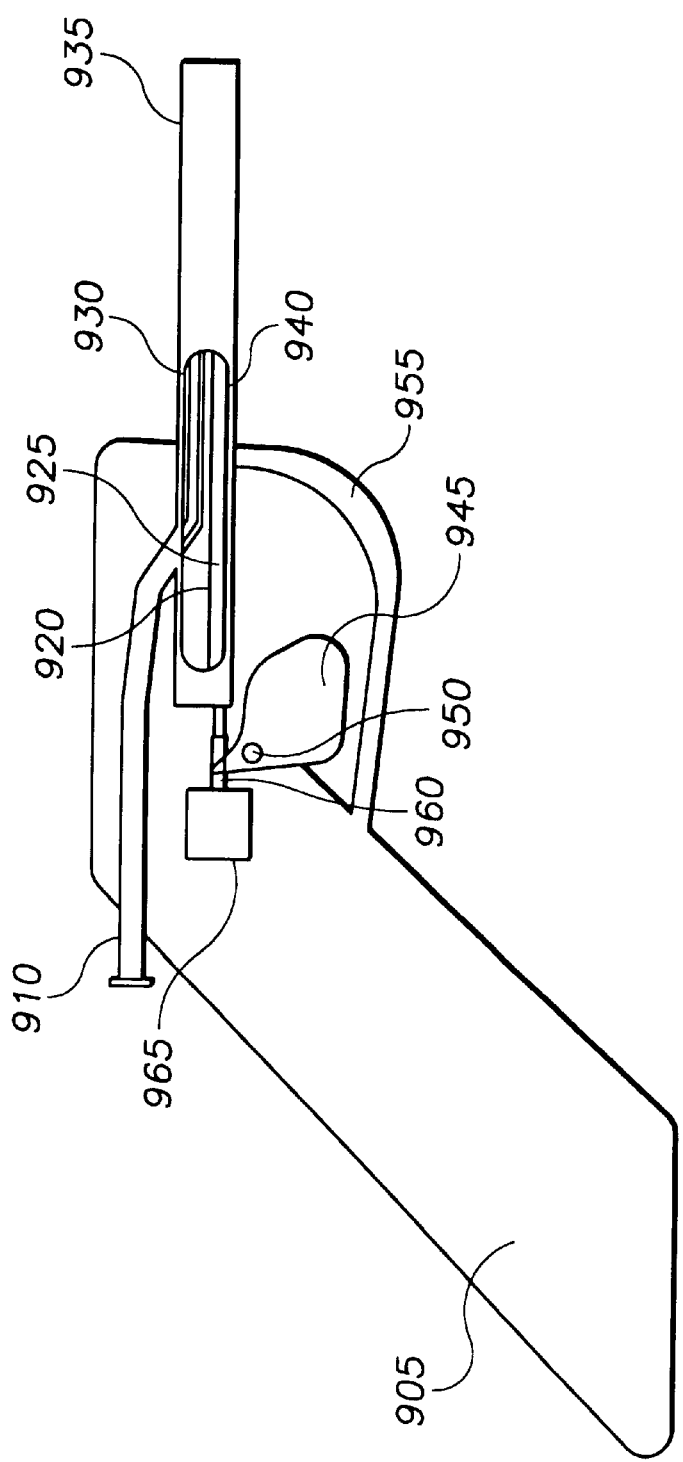

FIG. 9 shows a handpiece and a proximal operating mechanism for the catheter illustrated in FIG. 8. The catheter body proximal segment 920 corresponds to the catheter body distal segment 820 of FIG. 8. Here stylet knob 945 shows stylet fitting 960 engaged with trigger 945 which, when pulled proximally, forces the stylet fitting 960 to move axially a set amount as trigger 945 rotates about pivot 950. The stylet is completely removable, and is positioned in fitting 960 to effect deployment of a distally penetrating element once trigger is depressed. The stylet may have a number of regions that would engage stylet fitting 960 at different locations a few millimeters apart so that the amount of axially movement of stylet 925 within coil 920 may be controlled. Luer fitting 910 is positioned so that a small syringe may be attached and depressed with the thumb while the forefinger deploys the penetrating drug delivery element with the trigger 945. Cut away section marked as item 940 shows the drug delivery tubing running parallel to stylet coil 920 within catheter body 935. In other embodiments, a multi-lumen design may also be used.

In the preferred embodiments of the systems shown in FIGS. 8 and 9, the catheter body is preformed to effect a different location within the heart. Such a catheter will not require guiding catheters or steerability to effect its location. Such a catheter body could be adapted to have an additional lumen which runs its length to help facilitate its introduction into the heart by use of a guidewire which the catheter would be advanced over. In the preferred embodiment the preformed shape is such that the guidewire and its lumen are not necessary.

Numerous therapeutic agents may be injected into the heart with the catheters described above. These agents include small molecules, macromolecules, liposomal encapsulations of molecules, micro-drug delivery system encapsulation or covalent linking of carbohydrates and other molecules to a therapeutic molecules, as well as gene therapy preparations. These will be briefly defined.

"Small molecules" may be any smaller therapeutic molecule, known or unknown. Examples of known small molecules relative to cardiac delivery include the antiarrhythmic agents that affect cardiac excitation. Drugs that predominantly affect slow pathway conduction include digitalis, calcium channel blockers, and beta blockers. Drugs that predominantly prolong refractoriness, or time before a heart cell can be activated, produce conduction block in either the fast pathway or in accessory AV connections including the class IA antiarrhythmic agents (quinidine, procainimide, and disopyrimide) or class IC drugs (flecainide and propefenone). The class III antiarrhythmic agents (sotolol or amiodorone) prolong refractoriness and delay or block conduction over fast or slow pathways as well as in accessory AV connections. Temporary blockade of slow pathway conduction usually can be achieved by intravenous administration of adenosine or verapamil. [Scheinman, Melvin: Supraventricular Tachycardia: Drug Therapy Versus Catheter Ablation, Clinical Cardiology Vol 17, Suppl. II–11–II–15 (1994)]. Many other small molecule agents are possible, such as poisonous or toxic agents designed to damage tissue that have substantial benefits when used locally such as on a tumor. One example of such a small molecule to treat tumors is doxarubicin.

A "macromolecule" is any large molecule and includes proteins, nucleic acids, and carbohydrates. Examples of such macromolecules include the growth factors, Vascular Endothelial Growth Factor, basic Fibroblastic Growth Factor, and acidic Fibroblastic Growth Factor, although others are possible. Examples of macromolecular agents of interest for local delivery to tumors include angiostatin, endostatin, and other anti-angiogenic agents.

A "Liposome" refers to an approximately spherically shaped bilayer structure comprised of a natural or synthetic phospholipid membrane or membranes, and sometimes other membrane components such as cholesterol and protein, which can act as a physical reservoir for drugs. These drugs may be sequestered in the liposome membrane or may be encapsulated in the aqueous interior of the vesicle. Liposomes are characterized according to size and number of membrane bilayers.

A "gene therapy preparation" is broadly defined as including genetic materials, endogenous cells previously modified to express certain proteins, exogenous cells capable of expressing certain proteins, or exogenous cells encapsulated in a semi-permeable micro device. This terminology is stretched beyond its traditional usage to include encapsulated cellular materials as many of the same issues of interstitial delivery of macrostructures apply.

The term "genetic material" generally refers to DNA which codes for a protein, but also encompasses RNA when used with an RNA virus or other vector based upon RNA. Transformation is the process by which cells have incorporated an exogenous gene by direct infection, transfection, or other means of uptake. The term "vector" is well understood and is synonymous with "cloning vehicle". A vector is non-chromosomal double stranded DNA comprising an intact replicon such that the vector is replicated when placed within a unicellular organism, for example by a process of transformation. Viral vectors include retroviruses, adenoviruses, herpesvirus, papovirus, or otherwise modified naturally occurring viruses. Vector also means a formulation of DNA with a chemical or substance which allows uptake by cells. In addition, materials could be delivered to inhibit the expression of a gene. Approaches include: antisense agents such as synthetic oligonucleotides which are complimentary to RNA or the use of plasmids expressing the reverse compliment of a gene, catalytic RNA's or ribozymes which can specifically degrade RNA sequences, by preparing mutant transcripts lacking a domain for activation, or over express recombinant proteins which antagonize the expression or function of other activities. Advances in biochemistry and molecular biology in recent years have led to the construction of recombinant vectors in which, for example, retroviruses and plasmids are made to contain exogenous RNA or DNA respectively. In particular instances the recombinant vector can include heterologous RNA or DNA by which is meant RNA or DNA which codes for a polypeptide not produced by the organism susceptible to transformation by the recombinant vector. The production of recombinant RNA and DNA vectors is well understood and need not be described in detail.

Details on micro-encapsulated cells are described in U.S. Pat. No. 5,698,531 and additional details on the delivery of genetic material are described in U.S. Pat. No. 5,704,910. Both of these patents describe the potential of delivering such agents endoluminally within a blood vessel. Neither of these provides a means to deliver such agents at a depth within the heart muscle, and neither of them recognizes the potential of this approach. U.S. Pat. No. 5,661,133 does recognize the potential for delivering genes to the heart, but does not describe the means of delivery other than by injection.

Although the preferred embodiment of this invention is the delivery of the actual therapeutic molecules at a depth within the heart, it is also possible to deliver therapeutic molecules from micro drug delivery systems such as liposomes, nanoparticles, biodegradable controlled release polymer matrices, and biodegradable microspheres which are well known in the literature. Delivery matrices for heart disease should not alter the pharmacodynamics of the drug delivered, and adverse side effects of the matrices such as degradation mechanisms should be considered. There are many natural and synthetic matrices, such as FDA approved polylactide glycolide. PLGA polymers are available in a range of sizes and molecular weights. [Miller et. al. J. Biomed. Res. 11, 711 (1977).

Microspheres such as Alkerme's {Cambridge, Massachusetts} Prolease system enables freeze dried protein powder to be homogenized in organic solvent and sprayed to manufacture microspheres in the range of 20 to 90 um. The methods and devices required for delivery of such microspheres to a depth within the heart wall is an aspect of this invention. Development of such microsphere depots for sustained release of proteins with unaltered integrity requires methods to maintain stability during purification, storage, during encapsulation, and after administration to a depth within the heart tissue. Many of these techniques have been recently summarized in the literature. [Scott D. Putney, and Paul A. Burke: Improving protein therapeutics with sustained release formulations, Nature Biotechnology, Volume 16, February 1998, 153–157.] The value of delivering microsphere encapsulated macromolecular agents such as proteins bFGF and VEGF to a depth within the heart muscle for controlled release have not been described, and have substantial unrecognized benefits over other delivery approaches. The same catheter systems and methods for delivery of such microsphere encapsulated agents may be used for delivering gene therapy preparations.

It is intended that the inventions described herein may be used with guiding catheters, and as such a brief review is given. Guiding catheter use is straightforward and well known. For left ventricular delivery of agents, the guiding catheter is advanced within the arterial system carefully and its position is confirmed with appropriate medical imaging markers on the catheter, such as radio-opaque markers for fluoroscopy and ultrasound markers for echocardiography. Other markers for newer imaging modalities are also possible and easily incorporated. The guiding catheter is positioned so that its distal most tip is in the higher regions of the left ventricle such that a second catheter for drug delivery may be guided near or in contact with the delivery site. Introduction of catheters into the left ventricle and maneuvering within the heart chamber have been known to cause ventricular ectopy, and care should be taken to watch for ventricular tachycardia and ventricular fibrillation. Care in positioning the catheter so that it does not mechanically introduce such arrhythmias is important. LV guiding catheters may be placed across the aortic valve into the LV cavity over standard angiography pigtail catheters or over a standard guide wire approximately 0.035" in diameter. The guiding catheter will enable advancement of a centrally placed catheter through its internal lumen. Additional positioning of the drug delivery catheter within the targeted region can be achieved by small rotations of the guiding and/or drug delivery catheter.

There are generally two types of guiding catheter. The guiding catheter may be a steerable system as described in U.S. Pat. No. 5,030,204 or it may be a preformed shape as described in U.S. Pat. No. 5,722,400. Further other shapes for catheters which transverse the aorta in retrograde fashion are described in U.S. Pat. No. 5,016,640. Such guiding catheters are often formed with composite braided steel co-extruded polymer tubing because of its excellent torque transmission capabilities. If the guiding catheter is steerable, the implanting surgeon can have more control of the location of the distal tip because a second degree of bending freedom will have been added.

In other embodiments, the catheter could be advanced to the appropriate region of the left ventricle using trans-septal techniques. It should also be noted that all of these approaches are viable for reaching the right atrium, right ventricle, left atrium, and left ventricle of the heart in addition to other organs and tissues that can be accessed through body passageways. Focus of this discussion upon the left ventricle is not meant to limit the applicability of the devices and methods disclosed. In certain embodiments, where the drug delivery catheter has a preformed shape to access a specific regions of the heart and has a deployable penetrating structure, or when the drug delivery catheter is steerable, the need for the guiding catheter may be eliminated.

The drug delivery systems described for acute use have many other applications. They may be used as diagnostic catheters during an cardiac EP procedure, they could be used to deliver radio-opaque materials such as contrast media Renographin to determine if a particular site is appropriate for delivery of agents, or used to determine and evaluate flow characteristics under fluoroscopy. Likewise these systems could be designed for implantable use with appropriate material selection, and removal of aspects of the embodiment that would affect the device longevity in flexure, such as stylets.

Further, the drug delivery systems described here could be used acutely during beating heart cardiac surgery to introduce a temporary stop or marked slowing of the heart. Such induced bradycardia would provide a quiescent heart for very short periods so that delicate surgical procedures may be performed. Procedures as common and important as suturing during bypass surgery are one example of techniques that would be improved by such slowing of the heart. One example of implementation of this approach would involve a infusion of adenosine at a depth within the heart tissue adjacent to the AV node or infranodal structures with acute versions of the catheters described, followed after the quiescent period with temporary ventricular pacing to control haemodynamics. Additional agents could be given systemically to slow ventricular automaticity and the delivery of agents to introduce AV nodal blockade or infranodal blockade to result in a more marked slowing of the heart that could be rapidly reversed with ventricular pacing. The use of the catheter systems and local drug delivery schemes described in this disclosure are relevant for transient delivery for such slowing of the heart for improvement of surgical procedures.

In addition, the shear stress that will result on particles in slurry delivered through the inner diameter of the penetrating delivery structure and delivery tubing can be manipulated and controlled. The smaller the fluid pathway defined by the tubing and bore of the penetrating drug delivery structure, the greater the shear stresses. Awareness of this issue will enable appropriate sizing of the fluid pathways to facilitate the delivery of stress sensitive agents such as liposomes, microspheres, gene therapy preparations, proteins, and cellular materials. Further, delivering agents slowly over a period of time measured in seconds to minutes will reduce the size of these stresses.

These delivery systems could be left in for a period of minutes after delivery to minimize leakage of the agents delivered through the access site through the endocardium, and micro-drug delivery systems such as microspheres could be sized so that their leakage would not result in stroke if they leaked into the heart chamber. In addition, fluids could be delivered after the therapeutic macromolecules and macrostructures have been delivered to provide a means to redistribute them within the interstitium and prevent their flowing back into the heart chamber after the catheter is removed.

For delivery to the myocardial interstitium, the timing of the delivery could be gated by an electrically controlled pressure source to infuse only during the systole, or cardiac contraction, just as infusion could be gated to occur only during diastole, or cardiac relaxation. This is an important point, as the interstitial pressures will vary for this tissue and the tissue distribution will be altered. As different distributions may be required, the control of therapeutic agent delivery with cardiac timing can be important for different molecules. The torque coil presented in many embodiments is connected to electrically conductive penetrating elements which may be used to sense cardiac signals for this purpose.

Further, for systems where rapid delivery and repositioning is required, the torque coil could be advanced and retracted by a bi-directional DC motor unit attached to the handpiece, and the steerable structure could have different positions where it locks into place with a clicking mechanism such that the therapy could be delivered repeatably to a series of locations at the different bend geometries.

Thus the reader will see that the different embodiments of the invention provide a means to effectively deliver therapeutic agents to a depth within body tissues, and that a variety of procedures may be accomplished with these devices. Accordingly, the scope of the invention should be determined not by the embodiments illustrated, but by the appended claims and their legal equivalents.

I claim:

1. A catheter comprising:

an outer catheter body having a retractable sheath, a proximal end and a distal end;

one or more mechanical pull wires, disposed within the outer catheter body, for steering the catheter body;

a penetrating tubular element disposed within the retractable sheath of the outer catheter body;

one or more pull wires attached to the retractable sheath for retracting the sheath to expose the penetrating tubular element; and a delivery tube running from the proximal end of the outer catheter body to the distal end of the outer catheter body and in communication with the penetrating tubular element.

2. The device of claim 1, wherein the penetrating element is adapted to penetrate tissue within the body.

3. The device of claim 1, wherein the penetrating element is a needle.

4. A catheter comprising:

a catheter having a distal end and a proximal end;

a chamber for holding a therapeutic agent, the chamber disposed within the distal end of the catheter, the chamber having a self-sealing wall which is penetrable by an injection needle;

a penetrating element extending distally from the chamber; and a pressure source for forcing the therapeutic agent out of the chamber through the penetrating element.

5. The device of claim 4, wherein the penetrating element is adapted to penetrate tissue within the body.

6. The device of claim 4, wherein the penetrating element is a needle.

* * * * *